United States Patent [19]

Mossman

[11] Patent Number: 4,675,456
[45] Date of Patent: Jun. 23, 1987

[54] CATALYTIC ETHERIFICATION OF PHENOLS TO ALKYL ARYL ETHERS

[75] Inventor: Allen B. Mossman, Naperville, Ill.

[73] Assignee: Amoco Corporation, Chicago, Ill.

[21] Appl. No.: 853,040

[22] Filed: Apr. 17, 1986

[51] Int. Cl.⁴ .............................................. L07C 41/09
[52] U.S. Cl. .................................... 568/630; 568/632; 568/658
[58] Field of Search ......................... 568/630, 632, 658

[56] References Cited

U.S. PATENT DOCUMENTS

| | | | |
|---|---|---|---|
| 2,487,832 | 11/1949 | Searle | 568/630 |
| 4,450,306 | 5/1984 | Eskinazi | 568/630 |
| 4,487,976 | 12/1984 | Farcasiu | 568/630 |
| 4,533,758 | 8/1985 | Wells et al. | 568/630 |

*Primary Examiner*—Howard T. Mars
*Attorney, Agent, or Firm*—John B. Goodman; William H. Magidson; Ralph C. Medhurst

[57] ABSTRACT

A process for etherifying phenols comprising reacting phenols at elevated temperature and pressure with a reactant selected from the group consisting of alcohol, ether and mixtures thereof in the presence of a catalyst comprising a sulfated oxide of a lanthanide series metal selected from the group consisting of the lanthanide series metals and mixtures thereof on a support.

9 Claims, No Drawings

CATALYTIC ETHERIFICATION OF PHENOLS TO ALKYL ARYL ETHERS

BACKGROUND OF THE INVENTION

1. Field of the Invention

The field of this invention relates to the catalytic alkylation of phenols to form alkyl aryl ethers.

2. The Prior Art

Heretofore it has been recognized that attendant with the development of a synthetic fuels industry there will be an increase in the volume of phenolic compounds which must be handled in processes for refining and/or using synthetic crude. It is well known that phenolic compounds are present in especially high concentrations when the source of the synthetic crude is biomass or coal.

For example, phenolic compounds, such as phenol, cresol and their homologues, present in raw coal naphtha contribute to its instability and also tend to poison catalysts used to reform these naphthas to increase their octane value. Before raw coal naphtha can be reformed to increase its octane value, it must be hydrorefined or refined with hydrogen to eliminate sulfur and nitrogen compounds present therein which would otherwise poison the reforming catalyst. If phenols are present in the raw naphtha during the hydrorefining operation, the oxygen present in the phenolic hydroxyl groups results in a hydrogen debit with no significant increase in the octane value of the naphtha. On the other hand, the corresponding alkyl aryl ethers of phenol or phenols, such as anisole, are useful blending agents for improving the octane value of coal-derived naphthas. Therefore, it would be advantageous to etherify the phenols derived from such naphthas.

Catalytic etherification of phenols with low molecular weight alkyl alcohols, for example etherification of phenol with methanol to form anisole, was known heretofore. For example, U.S. Pat. No. 2,487,832 to Searle discloses that "solid dehydrating catalyst", such as activated aluminas, and the oxides of thorium, tungsten, titanium, zirconium, molybdenum and chromium, can catalyze the etherification of phenol. U.S. Pat. No. 4,487,976 to Farcasio discloses that sulfated transition metal oxides, for example tungsten and hafnium, can catalyze the etherification of phenol and U.S. Pat. No. 4,450,306 to Eskinazi discloses that $La_2(HPO_4)$, $Sr(HSO_4)_2$ and $Ba(HSO_4)_2$ can catalyze the etherification of phenols. While processes involving these catalysts may have merit, it would be desirable to have available other processes involving new catalysts which can present an opportunity to optimize the catalytic etherification of phenol.

A problem with the etherification of phenols with alcohols is the concurrent alkylation of the aromatic ring. Although the main product of ring methylation of phenol by methanol is ortho-cresol, the formation of 2,6-xylenol can also occur. These ring methylated products have all the undesirable properties of phenol with respect to poisoning reforming catalysts, etc. Therefore, a good etherification catalyst should not only provide high conversion of phenols to ethers, but also should be more selective to oxygen methylation than to ring methylation. In addition, a good etherification catalyst should be one that can be easily formulated from readily available materials.

SUMMARY OF THE INVENTION

It has now been found that phenols can be etherified by contacting a phenolic feed with a reactant selected from the group consisting of an alcohol, ether and mixtures thereof in the presence of a catalyst comprising a sulfated oxide of a lanthanide series metal selected from the group consisting of the lanthanide series metals and mixtures thereof on a support.

DETAILED DESCRIPTION OF THE INVENTION

Broadly stated, this invention is a process for etherifying phenols comprising reacting phenols at elevated temperature and pressure with a reactant selected from the group consisting of alcohol, ether and mixtures thereof in the presence of a catalyst comprising a sulfated oxide of a lanthanide series metal selected from the group consisting of the lanthanide series metals and mixtures thereof on a suitable support. Cerium is a preferred lanthanide series metal. Preferably the catalyst will include an alkali promoter selected from the group comprising of potassium, lithium, sodium, and mixtures thereof.

The phenols employed in the process of the invention can include phenol, cresols, xylenols, naphthols and other substituted phenols, for example, substituted phenols found in coal liquids. The alcohols employed in the process of the invention can include any alcohol capable of etherifying phenols. Generally $C_1$ to $C_4$ alcohols are preferred. Examples of such preferred alcohols are methanol, ethanol, propanol and mixtures thereof. Methanol is the most preferred reactant. A variety of ethers can be employed as a reactant in the process of the invention to etherify phenols. Any ether capable of etherifying phenols can be employed as a reactant. An example of a suitable ether is dimethylether. Suitable ratios of phenols to reactants can be from about 0.1 to about 20 on a weight basis. Preferably an excess of reactant is employed.

In accordance with the process of this invention the phenols and etherifying reactants are contacted at elevated temperatures and pressures. Suitable temperatures can be from about 100° C. to about 600° C., preferably from about 200° C. to about 500° C. Suitable pressures can be from about 25 to about 1500 psig, preferably from about 50 to about 700 psig.

The phenols and etherifying reactant in the presence of the catalyst of the invention are reacted for a time sufficient to etherify at least a portion of the phenols. In a stirred reactor, for example, suitable periods of time can be from about 0.2 to about 100 seconds. In a preferred process mode gaseous phenols and reactant are passed continuously through a fixed bed reactor. In such a preferred process, gas hourly space velocities (GHSV) in the range of from about 10 to about 10,000, preferably from about 100 to about 5,000, can be employed. The phenols/reactant gas hourly space velocity is a measure of the volume of phenols and reactant at standard temperature and pressure passing a given volume of catalyst in one hour.

Suitable supports include basic oxides, alumina, silica, carbon, or suitable solid compounds of magnesium, calcium, strontium, and barium. The silicas include, for example, silica gel, diatomaceous earth, and crystalline silicates. Preferably the support is porous and has a relatively high surface area. For example, very suitable supports can have a surface area from about 20 to about 1,000 square meters per gram and a pore volume of from about 0.8 to 1.2 cc per gram. Especially preferred supports have a surface area in the range of from about 150 to about 250 square meters per gram and a pore volume in the range of from about 0.8 to about 1.2 cc per grams. An example of a preferred support is a relatively high surface area of alumina having a surface area and pore volume in the preferred range.

The catalyst composition employed in the process of the invention can be prepared by any of the well-known techniques such as impregnation, coprecipitation, incipient wetness and the like. If, for example, the incipient wetness technique is employed, a water soluble lanthanide series metal salt is dissolved in the minimum amount of water or an amount of water sufficient to fill the internal volume of the catalyst support at least once. This solution is then impregnated on the catalyst support followed by drying and reimpregnation until the total sample has been deposited on the support. Sufficient sulfuric acid is then impregnated on the catalyst support to convert the lanthanide series metal salt to its sulfate form. This material is then calcined in air, for example, at 1,000° F. for 4 hours. An alternative method involves the addition of the sulfuric acid to the solution of the lanthanide series metal salt being used, and the impregnation of this solution on the catalyst support. Another alternative method involves the impregnation of lanthanide series metal sulfate solution on to the catalyst support. Other well-known catalyst preparation techniques can be employed to prepare suitable catalyst compositions of the invention.

The lanthanide series metal loadings can range from about 0.05 to 25 weight percent metal based on the total weight of the catalyst, preferably from about 0.5 to about 10 weight percent and more preferably from about 1.5 to about 5 weight percent. Preferably an amount of alkali promoter is included in the catalyst. The alkali promoter can be included in various amounts and in a variety of ways. For example, a very suitable manner for including the alkali promoter is to impregnate a solution of alkali metal hydroxide on the catalyst support used in the preparation of the lanthanide series metal catalyst composition of the invention.

As mentioned hereinbefore, the preferred support is a high surface area alumina. This support including the lanthanide series metal sulfate is the preferred catalyst employed in the process of the invention. This catalyst of the process of the invention is highly advantageous in that it is formed from readily available lanthanide series metals, for example, cerium, and the catalyst provides excellent conversion and selectivity towards etherification of phenols.

The following examples are provided to better illustrate the invention by presenting several specific embodiments of the process of the invention.

EXAMPLE I

Part A (Catalyst Preparation)

A cerium metal catalyst of this invention was prepared in the following manner:

Ceric sulfate (2.91 gm) was dissolved in 150 cc 4% sulfuric acid. This solution was impregnated on alumina (25 gm; 20–40 mesh). The impregnated alumina was dried at 110° C. in air and the impregnation was repeated until the total solution was deposited on the alumina support. The catalyst was then calcined under programmed conditions (4 hr at 200° F., heating at increasing temperature at a rate of 200° F./hr for 4 hr, and holding for 4 hr at 1000° F.). The catalyst was then vacuum sieved to remove any fines and used as such in the etherification process.

Part B (Etherification Process at Varying Temperatures)

The catalyst was loaded into a tubular reactor of approximately 0.37 inch inside diameter. Enough catalyst was added (12.5 cc) to produce a 15 cm bed. The bed was then heated to the various temperatures indicated in Table I below. A solution of phenol in methanol (1 to 4 mole ratio) was passed over the catalyst bed at a rate of 1 cc/min. Pressure was maintained at 50 to 55 psig. The product from the reaction was collected and analyzed by gas liquid chromatography. The percent conversion obtained as anisole and as all ethers (including anisole) at various temperatures is indicated in Table I below.

TABLE I

| Temp °C. | Conversion % | Anisole % | Ethers % | Selectivity Anisole % | Selectivity Ethers % |
|---|---|---|---|---|---|
| 250 | 3.0 | 3.0 | 3.0 | 100 | 100 |
| 300 | 38.0 | 36.4 | 37.7 | 95.1 | 98.5 |
| 350 | 55.1 | 22.0 | 28.7 | 40.0 | 52.0 |
| 400 | 78.7 | 1.6 | 5.9 | 2.1 | 7.5 |

As can be seen from Table I, excellent conversion of phenols to ether is obtained when employing the preferred temperature ranges of the invention. In cases set forth above selectivity to ethers is high.

Optimum temperatures to obtain optimum conversion and/or selectivity for particular phenolic feeds and/or particular reactants can be determined in a routine manner by employing procedures such as illustrated in Example I.

EXAMPLE II

Part A (Catalyst Preparation)

A cerium metal catalyst of this invention containing a promoter can be prepared in the following manner:

Potassium hydroxide (0.28 gm) is dissolved in water (20 gm). This solution is impregnated on alumina (25 gm; 20–40 mesh). The impregnated alumina is dried at 110° C. in air and the impregnation is repeated until the total solution is deposited on the alumina support. Ceric sulfate (1.28 gm) is dissolved in sulfuric acid. The ceric sulfate solution is then deposited on the alumina support in a similar manner. The catalyst is then calcined under programmed conditions (4 hr at 200° F., heating at increased temperature at a rate of 200° F./hr for 4 hr, and holding for 4 hr at 1000° F.). The potassium promoted cerium metal catalyst is then vacuum sieved to remove any fines and used as such in the etherification process.

Part B (Etherification Process)

When the potassium promoted cerium metal catalyst of Part A is employed in the etherification process set forth in Example II, Part B, good results are obtained in that there is excellent conversion of phenol to methyl ethers and excellent selectivity to ethers.

What is claimed is:

1. A process for etherifying phenols comprising reacting phenols at a temperature of from about 100° C. to about 600° C. and a pressure of from about 25 to 1500 psig with a reactant selected from the group consisting of $C_1$–$C_4$ alcohols, dimethyl ether and mixtures thereof in the presence of a catalyst comprising a sulfated oxide of a lanthanide series metal selected from the group consisting of the lanthanide series metals and mixtures thereof on a support.

2. The process of claim 1 wherein the catalyst includes a promoting amount of an alkali metal selected from the group consisting of potassium, lithium, sodium and mixtures thereof.

3. The process of claim 1 wherein the lanthanide series metal is cerium.

4. The process of claim 3 wherein the alkali metal is potassium

5. The process of claim 2 wherein the temperature is from about 200° C. to about 500° C.

6. The process of claim 2 wherein the pressure is from about 50 to about 700 psig.

7. The process of claim 3 wherein the alcohol is methanol.

8. The process of claim 1 wherein the reactant is dimethyl ether.

9. The process of claim 1 wherein the support is a high surface area alumina.

* * * * *